(12) United States Patent
Isola et al.

(10) Patent No.: US 9,295,443 B2
(45) Date of Patent: Mar. 29, 2016

(54) METHOD AND SYSTEM FOR REDUCING LOCALIZED ARTIFACTS IN IMAGING DATA

(71) Applicant: KONINKLIJKE PHILIPS N.V., Eindhoven (NL)

(72) Inventors: Alfonso Agatino Isola, Eindhoven (NL); Eberhard Sebastian Hansis, Hamburg (DE); Jens Wiegert, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 40 days.

(21) Appl. No.: 14/377,202

(22) PCT Filed: Feb. 18, 2013

(86) PCT No.: PCT/IB2013/051302
§ 371 (c)(1),
(2) Date: Aug. 7, 2014

(87) PCT Pub. No.: WO2013/124777
PCT Pub. Date: Aug. 29, 2013

(65) Prior Publication Data
US 2016/0007948 A1 Jan. 14, 2016

Related U.S. Application Data

(60) Provisional application No. 61/601,693, filed on Feb. 22, 2012.

(51) Int. Cl.
*G06K 9/00* (2006.01)
*A61B 6/00* (2006.01)
(Continued)

(52) U.S. Cl.
CPC ............... *A61B 6/5264* (2013.01); *A61B 6/032* (2013.01); *A61B 6/46* (2013.01); *A61B 6/5211* (2013.01); *G06K 9/46* (2013.01); *G06K 9/4604* (2013.01); *G06K 9/52* (2013.01); *G06K 9/6215* (2013.01); *G06K 9/6267* (2013.01); *G06T 5/00* (2013.01); *G06T 7/0012* (2013.01); *G06T 7/0081* (2013.01); *G06T 7/2033* (2013.01); *G06T 11/008* (2013.01); *G06K 2009/4666* (2013.01); *G06T 2207/10081* (2013.01); *G06T 2207/20141* (2013.01); *G06T 2207/20182* (2013.01);
(Continued)

(58) Field of Classification Search
CPC .................................... G06K 9/00; A61B 5/00
USPC ......... 382/128, 129, 130, 131, 132, 133, 134; 324/307; 348/666
See application file for complete search history.

(56) References Cited

U.S. PATENT DOCUMENTS 6,208,138 B1 * 3/2001 Lai ..................... G01R 33/3875
324/307
2003/0053671 A1 3/2003 Dewaele et al.

OTHER PUBLICATIONS

Ahmed, M. N., et al.; A Modified Fuzzy C-Means Algorithm for Bias Field Estimation and Segmentation of MRI Data; 2002; IEEE Trans. on Medical Imaging; 21(3)193-199.

*Primary Examiner* — Abolfazl Tabatabai

(57) ABSTRACT

A method and system for reducing localized artifacts in imaging data, such as motion artifacts and bone streak artifacts, are provided. The method includes segmenting the imaging data to identify one or more suspect regions in the imaging data near which localized artifacts are expected to occur, defining an artifact-containing region of interest in the imaging data around each suspect region, and applying a local bias field within the artifact-containing regions to correct for the localized artifacts.

34 Claims, 4 Drawing Sheets

(51) Int. Cl.
  *A61B 6/03* (2006.01)
  *G06T 7/00* (2006.01)
  *G06T 5/00* (2006.01)
  *G06K 9/46* (2006.01)
  *G06K 9/62* (2006.01)
  *G06T 7/20* (2006.01)
  *G06T 11/00* (2006.01)
  *G06K 9/52* (2006.01)
  *G01V 3/00* (2006.01)
  *H04N 9/78* (2006.01)

(52) U.S. Cl.
  CPC ................ *G06T2207/20201* (2013.01); *G06T 2207/30008* (2013.01)

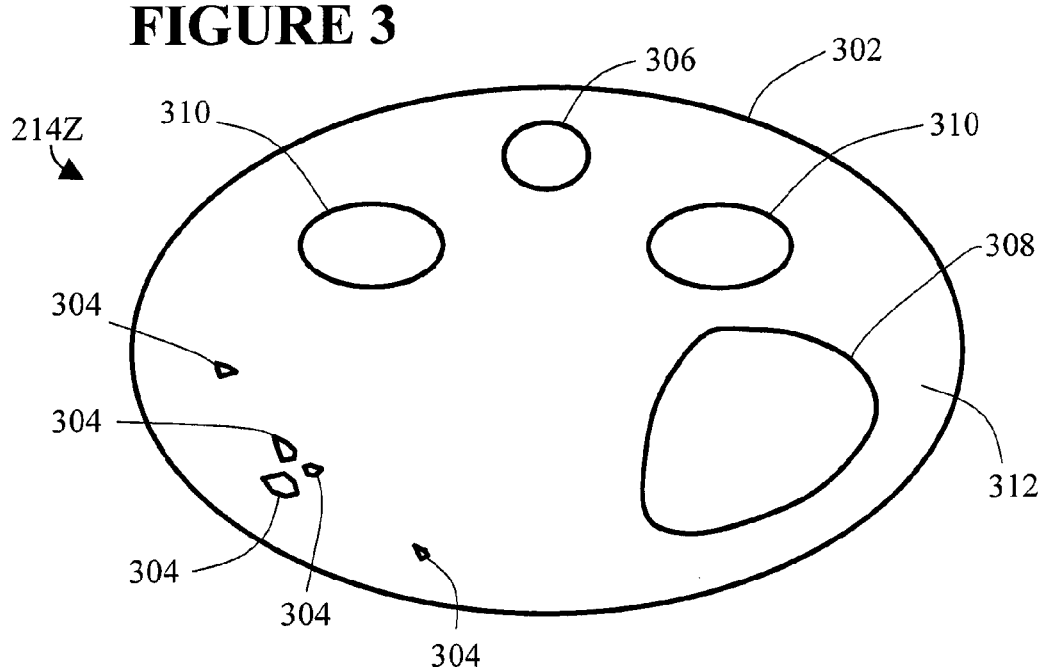
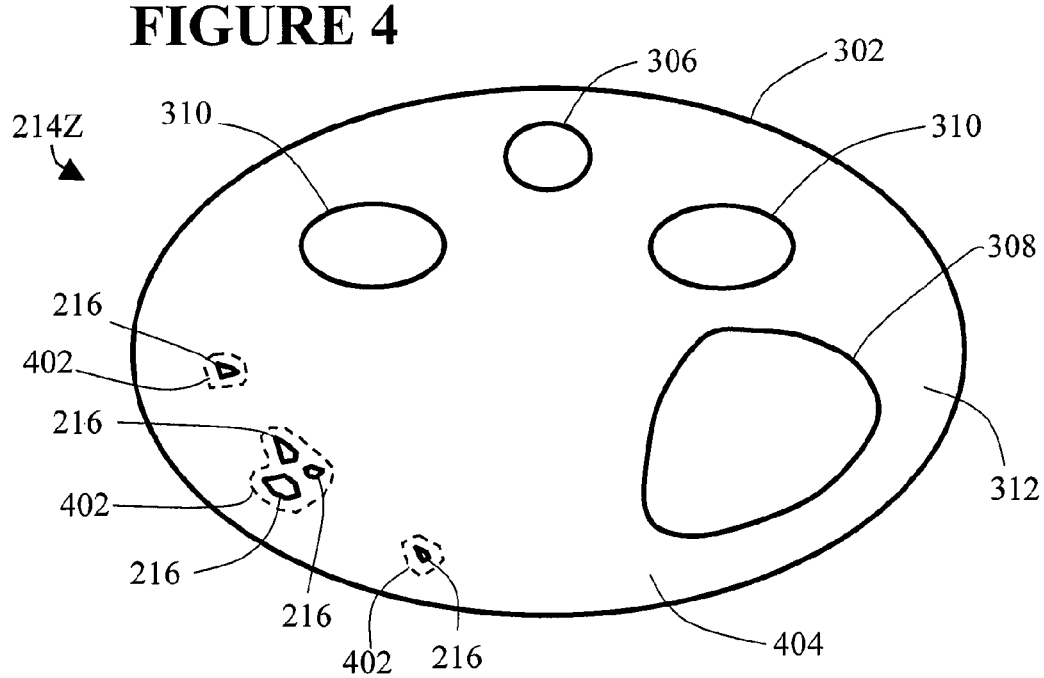

US 9,295,443 B2

1

METHOD AND SYSTEM FOR REDUCING LOCALIZED ARTIFACTS IN IMAGING DATA

CROSS REFERENCE TO RELATED APPLICATIONS

This application is a national filing of PCT application Ser. No. PCT/IB2013/051302, filed Feb. 18, 2013, published as WO 2013/124777 A1 on Aug. 29, 2013, which claims the benefit of U.S. provisional application Ser. No. 61/601,693 filed Feb. 22, 2012, which is incorporated herein by reference.

The present application relates generally to the imaging arts and more particularly to a method and system for reducing motion artifacts in medical x-ray computer tomography (CT) imaging. The application subject matter also finds use in other imaging systems where motion artifacts are a concern, such as for example general radiography (GR), magnetic resonance imaging (MR), nuclear medicine (NM), and combinations thereof. Nuclear medicine includes, for example, single photon emission computed tomography (SPECT) imaging systems and positron emission tomography (PET) imaging systems.

However, in its broader aspects, the application subject matter is not limited to the medical imaging field, and may apply to imaging systems in non-medical fields. These imaging systems typically gather imaging data regarding an object, such as a human person, and record that imaging data for later analysis and use. Such uses include for example medical diagnosis, tracking the growth or properties of a tumor within a person's body, looking for illegal or dangerous items such as guns and knives for security purposes, and the like. Thus, while one embodiment is medical imaging and much of the following description relates to the medical imaging field, the present invention applies in other fields as well.

Imaging studies often suffer from motion artifacts. This is a particular problem in cone-beam computed tomography (CBCT) studies recorded by combined SPECT/CT systems, or other radiotherapy systems, using a flat-panel x-ray detector. Such studies are often used for attenuation correction and localization of imaging data from the SPECT and CT imaging modalities, and also for target localization in image-guided radiotherapy. These CBCT systems typically have gantry rotation times on the order of several seconds or even a few minutes, which makes the imaging data sensitive to artifacts from patient motion. These artifacts distract the interpreting physician, lower confidence in the imaging study, and may impair the accuracy of attenuation correction.

Most voluntary patient motion can be controlled during the imaging acquisition by appropriate preparation of the patient within the imaging space, and instructing the patient to remain still while imaging data is being recorded. However, involuntary patient motion such as heart motion, breathing during longer imaging scans, bowel gas motion, and the like cannot be avoided so easily. In particular, the motion of gas pockets in the patient's bowel can cause strong motion artifacts. Therefore, a software solution to reduce involuntary motion artifacts is desirable.

Several approaches already exist to reduce motion artifacts during CBCT reconstruction and other imaging techniques. These include motion-compensated reconstruction, projection-based motion compensation, and others. In general, these known methods require estimating the shape and motion of the moving object(s). They often additionally rely on assumptions regarding the moving object(s), such as rigidity, smoothness, or periodicity of motion. Such known methods usually concern large object motion or periodic object

2 motion. They cannot easily be applied to bowel gas motion, where the moving air pockets are small, vary in shape, and move in unpredictable and non-smooth ways. Additionally, motion-compensated reconstruction and motion estimation are often very computationally demanding.

The presently described methods overcome these problems. They do not require an estimation of a motion vector field, and they can be applied to irregularly-shaped objects such as bowel gas pockets. The methods can be implemented on a purely post-reconstruction basis, making them computationally efficient. The methods lead to a visual reduction in motion artifacts and thereby improve the overall image quality, enhance the confidence in the study, and may increase the accuracy of attenuation correction for an accompanying SPECT study. Additionally, a measure of confidence can be derived and presented to the user, to identify imaging data regions which may possibly be affected by motion artifacts.

According to one aspect of the present invention, a method for reducing localized artifacts in imaging data is provided. The method comprises segmenting the imaging data to identify one or more suspect regions in the imaging data near which localized artifacts are expected to occur; defining an artifact-containing region of interest in the imaging data around each suspect region; defining one or more classes for the image data of the artifact-containing regions of interest, and associating each class with at least one representative imaging value; assigning each item of image data within the artifact-containing regions to one of the classes; determining a local bias field within the artifact-containing regions describing, for each item of image data within the artifact-containing regions, a difference between a calculated imaging value and the imaging representative value based on the classification; and applying the local bias field to the imaging data within the artifact-containing regions to produce an artifact-corrected imaging data. Corresponding systems are also provided. Additionally, a local measure of confidence can be determined to alert the user to possibly artifact-affected regions.

Numerous advantages and benefits will become apparent to those of ordinary skill in the art upon reading the following detailed description of several embodiments. The invention may take form in various components and arrangements of components, and in various process operations and arrangements of process operations. The drawings are only for the purpose of illustrating many embodiments and are not to be construed as limiting the invention.

FIG. 3 is a schematically representative illustration of segmented reconstruction data;

FIG. 4 is a schematically representative illustration of segmented reconstruction data including defined artifact-containing regions surrounding bowel gas pockets.

Figure 1:
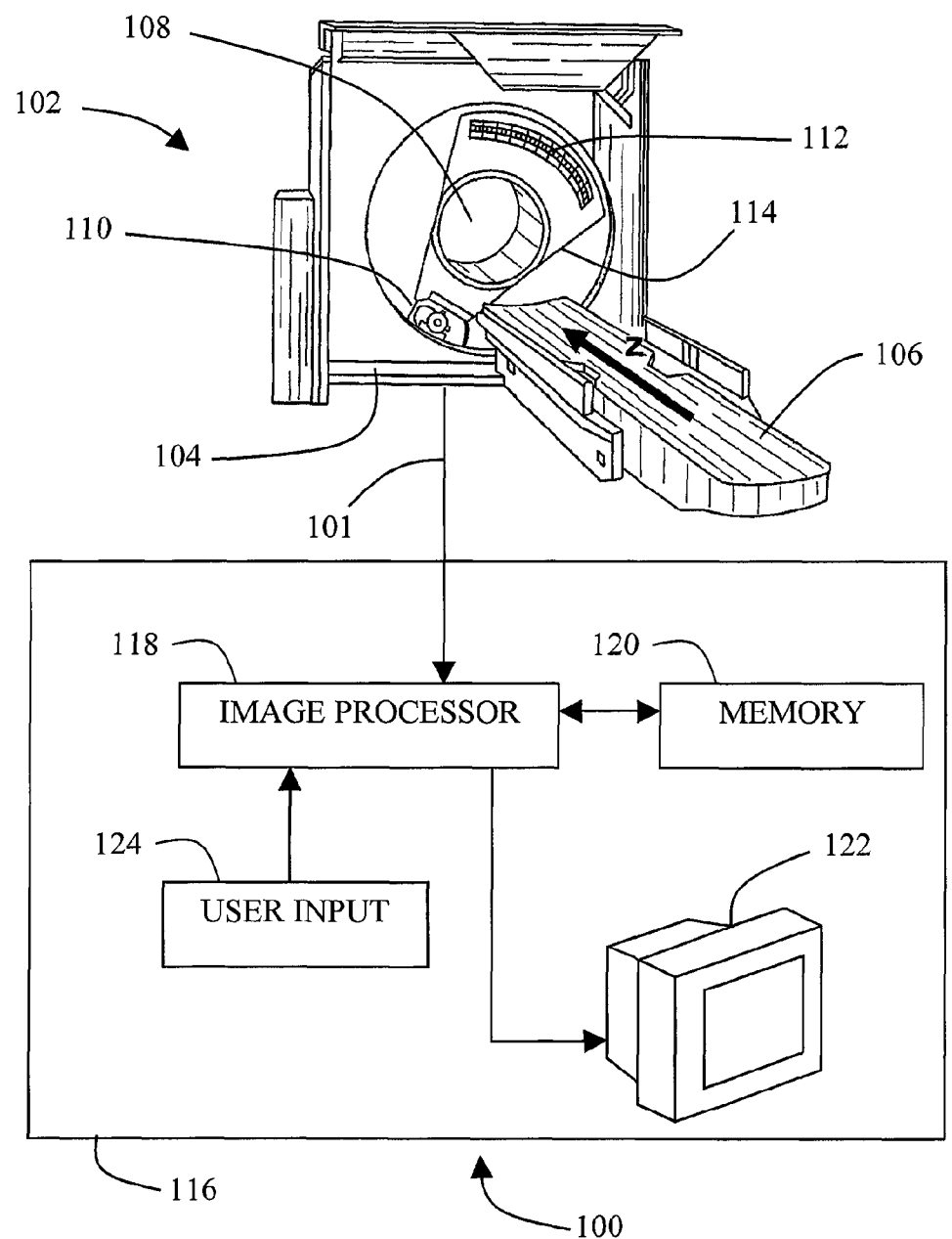
FIG. 1 is an exemplary medical CT imaging system 100, with a portion of the stationary gantry cut away to reveal the rotating x-ray source and data measurement system within the gantry.

The subject matter of the present disclosure finds use in connection with any imaging system in which motion artifacts are a concern, for example, a CT imaging system. More specifically, with reference to FIG. 1, in one embodiment the imaging system 100 is a medical CT imaging system. A CT imaging acquisition system 102 includes a gantry 104 and an object support 106 such as a table or couch which moves along the z-axis. A patient or other object to be imaged (not shown) lies or is placed down on the object support 106 and is moved to be disposed within an aperture 108 in the gantry 104. Once the patient or object is in position within the aperture 108, an x-ray source 110 emits a projection of x-rays to be gathered by an x-ray data measurement system 112 inside the gantry 104. (A portion 114 of the gantry 104 is cut away in FIG. 1 to show the x-ray source 110 and x-ray data measurement system 112 which are housed inside the gantry 104.) The x-ray source 110 and data measurement system 112 rotate together around the aperture 108 to acquire and record CT imaging data from various positions. In some embodiments such rotation may occur while the object support 106 is stationary. In other embodiments such rotation may occur in conjunction with linear movement of the object support 106 along the z-axis in a "helical" scan. The rotation is possible because the x-ray source 110 and the data measurement system 112 are each mounted to a common rotor (not shown) inside the gantry 104.

The data measurement system 112 of the CT imaging acquisition system 102 thus acquires CT imaging data in the form of detected x-rays. The system 102 then transfers the acquired CT imaging data on to a CT imaging, processing and display system 116 through a communication link 101. Although the systems 102 and 116 are shown and described here as being separate systems for purposes of illustration, they may in other embodiments be part of a single system. When the systems 102 and 116 are separate systems, the communication link 101 may be any link which permits the transfer of data between the systems, such as a Local Area Network, the Internet, a physical transfer of a memory storage medium such as a computer diskette, CD-ROM, or flash drive, or the like. The communication link 101 may be wired, wireless, or a combination thereof. Thus, the systems 102 and 116 may be located in different rooms, different buildings, or even different cities. Most typically, however, the systems 102 and 116 are either in the same room or in separate but adjoining and connected rooms. An operator may then use the system 116 to control the system 102 during the imaging acquisition process.

Via the communication link 101, the acquired CT imaging data passes to an image processor 118 which stores the acquired CT imaging data in a memory 120. The image processor 118 may apply well-known image reconstruction techniques to electronically process the acquired CT imaging data and generate reconstructed imaging data, comprising digital images of the imaged patient or other object. The image processor 118 can show the resulting reconstructed imaging data on an associated display 122. A user input 124 such as a keyboard and/or mouse device may be provided for a user to control the processor 118.

The imaging system 100 may be a stand-alone unit which provides only CT-based imaging, as is shown in FIG. 1. Although not shown here, the imaging system 100 may additionally include appropriate components for PET and/or SPECT imaging, or some other imaging modality, in conjunction with the CT-based imaging components. Also, although the exemplary system of FIG. 1 is a CT imaging system, the present method also applies to many other imaging systems such as PET systems, SPECT systems, MRI systems, and combinations thereof. All such systems have an imaging acquisition component (such as the CT system 102) and an imaging processing component (such as the CT system 116). The imaging acquisition component generates, measures and records one or more different kinds of acquired imaging data concerning an imaged subject. The imaging processing component receives the acquired imaging data and in some cases processes it to generate reconstructed imaging data which can be viewed on a display. In other cases, such post-acquisition processing may not be necessary in order to display the imaging data for review by users, or it might be performed at a later time by a different system.

Thus the functions described herein can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory such as memory 120, part of an operating system or other type of executable instructions. It will be appreciated by one of ordinary skill in the art that the form of software is dependent on, for example, requirements of a desired application, the environment it runs on, and/or the desires of a designer/programmer or the like.

The systems and methods described herein can be implemented on a variety of platforms including, for example, networked control systems and stand-alone control systems. Additionally, the logic shown and described herein preferably resides in or on a computer readable medium such as the memory 120. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

Typically, one or more technologists operate the imaging systems 102 and 116 to generate the acquired imaging data, and also perhaps to process the acquired imaging data to generate reconstructed imaging data. These technologists are qualified by their education, training and experience to operate the imaging systems and manipulate the imaging data.

Figure 2:
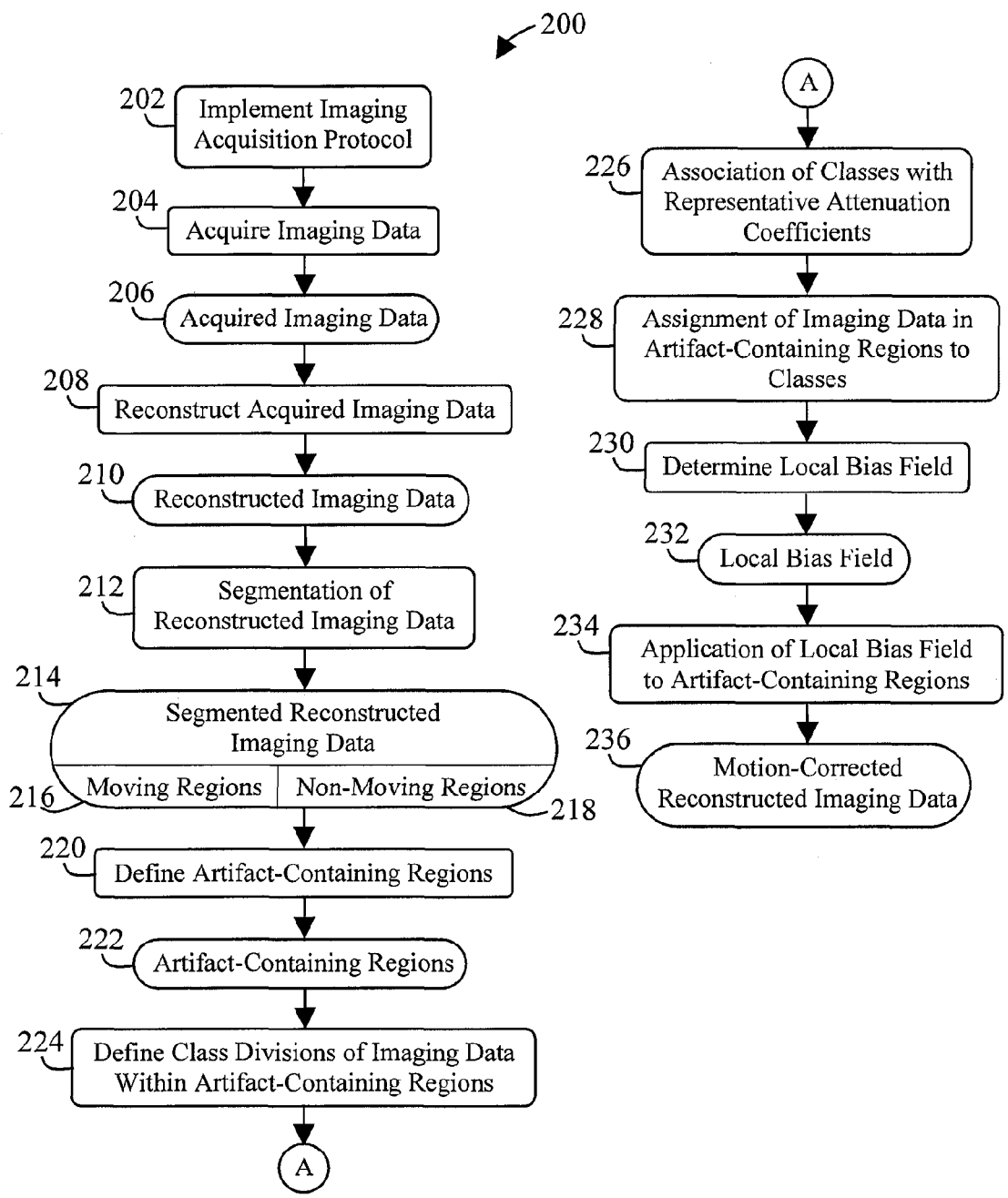
FIG. 2 illustrates an exemplary method 200 for reducing motion artifacts in imaging data.

Thus a method for reducing motion artifacts in imaging data is provided. An exemplary such method 200 is illustrated in FIG. 2. The method 200 starts with the technologist implementing 202 an imaging acquisition protocol. The protocol most often will follow a prescription which has already been determined by a medical doctor or other specialist who, in consultation with the patient, has determined that the imaging scan is advisable. The protocol defines the imaging scan to be implemented 202 to generate acquired imaging data 206. For example, the protocol may define the area(s) of the patient's body to image and the type of imaging scan to perform. In the exemplary embodiment of a medical CT imaging system 100 described above, the protocol will determine the movement of the object support couch 106, and of the x-ray source 110 and x-ray data measurement system 112, and the x-ray dosage to apply during an imaging scan. The technologist may often implement 202 any one or more of several wholly or partially pre-defined imaging acquisition protocols. In nuclear medicine imaging, implementing 202 the imaging acquisition protocol may involve either asking the imaged patient to ingest a radiopharmaceutical, or injecting the radiopharmaceutical into the bloodstream of the patient.

In the next step of the method 200, the imaging data is acquired 204. That is, the imaged subject is situated within the imaging apparatus and an imaging scan is performed to record acquired imaging data 206 according to the protocol.

The resulting acquired imaging data 206 may optionally be reconstructed 208. Depending on the imaging modality being utilized, the acquired imaging data 206 recorded directly by the imaging equipment during the acquisition scan 204 may or may not be the exact data of interest. In some cases, that acquired imaging data 206 may have to be processed using any one or more of many well-known "reconstruction" processes 208 to generate reconstructed image data 210 for use by medical professionals and the like. As one example, the x-ray transmission data acquired by the medical CT imaging system 100 typically needs to be reconstructed to generate medically useful data. Such reconstruction processes 208 include, for example, filtered backprojection methods, iterative methods, and other reconstruction methods. The reconstruction method 208 is often specialized to take into account the specific geometry of the imaging system being used, such as in the case of offset-detector CBCT reconstruction. The reconstructed imaging data 210 may be arranged into discrete items, such as for example two-dimensional pixels or three-dimensional voxels of imaging data. In the following discussion, it is assumed that the reconstructed imaging data 210 is three-dimensional. But the applicability of the methods described herein to the less complicated two-dimensional context should be readily apparent to one of ordinary skill in the art.

In many cases, the initial imaging acquisition protocol will specify the reconstruction process 208 used to derive reconstructed imaging data 210 from the acquired imaging data 206. In those cases, the two steps 204 and 208 may be operated at the same time. That is, while the imaging system is gathering acquired imaging data 206, it may concurrently apply the reconstruction method 208 to the already-acquired imaging data 206. In other cases, however, the initial imaging acquisition protocol may not include any reconstruction processes 208. In those situations, the reconstruction data processing 208 is determined and performed after the imaging acquisition 204 has been completed and the data 206 is entirely generated. Thus, the method 200 may be applied using an imaging data acquisition system such as the system 102, or a post-acquisition processing system such as the system 116.

The reconstruction step 208 is optional. In some situations, the directly acquired imaging data 206 may be sufficient on its own without needing reconstruction 208 to be useful for a medical diagnosis or for other whatever other purpose the imaging data 206 was acquired. In those situations, references to reconstructed imaging data 210 in the following discussion should be taken to refer to the directly acquired imaging data 206, without any reconstruction 208 being performed.

The reconstructed imaging data 210 is segmented 212 to identify portions of the reconstructed imaging data 210 which correspond to moving objects such as bowel gas pockets. The moving objects may be segmented 212 within the reconstructed imaging data 210 using known segmentation methods. For example, one known segmentation method 212 is to apply one or more thresholds to the reconstructed imaging data 210. That is, the radiodensity or attenuation coefficient values (often measured in Hounsfield units) assigned to each voxel in the three-dimensional reconstructed imaging data 210 are distributed among two or more different segmented groups of data based on defined ranges of minimum and maximum values. At least one of the data groups of segmented reconstructed imaging data 214 corresponds to moving objects such as bowel gas pockets. Other potential data groups of segmented reconstructed imaging data 214 include soft tissue, bone, air pockets in the lungs, or other kinds of regions which may be of interest in the particular study being conducted. Many segmentation methods are known. Whichever segmentation method is applied, the reconstructed imaging data 210 is segmented 212 into various data groups and corresponding regions of interest.

The initial threshold segmentation may be supplemented by a region growing segmentation step as part of the overall segmentation 212. That is, the initial regional classifications are used as seed points, which are then modified based on the characteristics of the immediately surrounding areas within the imaging data 210. Knowledge about the feature of interest, such as the size or location of the bowel gas pockets, can augment the segmentation 212 and help to differentiate bowel gas pockets from other air pockets located in the lungs or outside of the patient's body. For example, bowel gas pockets will be located below the patient's diaphragm, and under the patient's skin.

FIG. 3 is a schematically representative illustration of segmented reconstructed imaging data 214. FIG. 3 represents a two-dimensional cross-section 214Z of the three-dimensional segmented reconstructed imaging data 214 of a patient 302, taken perpendicular to the z-axis of FIG. 1. The imaging data 214Z is segmented 212 into various regions, including bowel gas pockets 304, bone 306 (the patient's spine), liver 308, and kidneys 310, with the remainder characterized simply as soft tissue 312. The other portions of the three-dimensional segmented reconstructed imaging data 214, at different z-axis values, may be similarly segmented using the same methods.

Returning to the description of FIG. 2, each of the regions within the segmented reconstructed imaging data 214 is classified as a "moving" region 216 or a "non-moving" region 218. These are relative, rather than absolute, classifications. That is, regions classified as moving regions 216 in the segmented reconstructed imaging data 214 correspond to objects which are suspected to cause motion artifacts. Any regions which do not qualify as moving regions 216 are then classified as non-moving regions 218. So, objects which appear in non-moving regions may very well be objects which are moving, but just not quickly enough to cause motion artifacts for example. Indeed, the simplest segmentation 212 is a binary segmentation between suspect moving regions 216 and all other imaging data 218.

In the particular example of FIG. 3, the only objects which are suspected to cause motion artifacts are the bowel gas pockets 304. Therefore, in the illustrated imaging data 214Z, the moving regions 216 correspond to the collection of the bowel gas pockets 304. And, the non-moving regions 218 correspond to the collection of bone 306, liver 308, kidneys 310, and soft tissue 312 regions.

The next step of the method 200 defines 220 artifact-containing regions of interest 222 around each moving region 216. Motion artifacts are assumed to originate from the moving regions 216. Therefore, it is to be expected that the motion artifacts are generally decreasing in magnitude with increasing distance from the suspect moving regions 216. Thus, the step 220 seeks to define the portions of the segmented reconstructed imaging data 214 which may be affected by motion artifacts. The inner boundary or boundaries of each artifact-containing region 222 correspond(s) to the suspect moving regions 216 identified in the segmentation step 212. The outer boundary of each artifact-containing region 222 is determined by the step 220.

The artifact-containing regions of interest 222 may be defined 220, for example, by region growing using the suspect moving regions 216 as seed points. The stopping criterion for the region growing is designed to differentiate between regions affected by motion artifacts and regions not affected by motion artifacts. As an example, a simple stopping criterion may define a "normal" range of attenuation coefficient values for the tissue which surrounds the suspect moving regions 216. Then, the artifact-containing regions of interest 222 are defined by region growing out from the suspect moving regions 216 until an entire outer border of normal attenuation coefficient values is encountered. Additional stopping criteria may alternatively or additionally be employed. The artifact-containing region definition step 220 may also account for other properties of the artifact-containing regions 222, such as spatial connectivity, outline smoothness, expected shape of the artifacts, general knowledge about the anatomy in the areas of interest, and knowledge about typical attenuation coefficients of different tissue types in the segmented data 214.

In the specific example of FIG. 3, the tissue which immediately surrounds the moving regions 216 is all segmented as soft tissue 312. Thus, in that example, a normal range of attenuation coefficient values for soft tissue may be utilized as the stopping criterion. An additional stopping criterion might be an encounter with a different segmentation region, such as air 304, bone 306, liver 308, kidney 310, or any other segmentation region which is not soft tissue 312.

FIG. 4 is a schematically representative illustration of segmented reconstructed imaging data 214 including defined artifact-containing regions. FIG. 4 is the same two-dimensional cross-section 214Z as shown in FIG. 3. In FIG. 4, the data 214Z is divided into three classes: the suspect moving regions 216, the artifact-containing regions 402, and the artifact-free regions 404. The suspect moving regions 216 comprise each of the regions from the segmentation 212 that were classified as moving regions 304. In the particular example of FIGS. 3 and 4, only the bowel gas pockets 304 were defined as suspect moving regions 216. Each of those suspect moving regions 216 is then surrounded by artifact-containing regions 402 as determined in step 220, which are shown by dotted lines in FIG. 4. Then, all other imaging data which is not in a suspect moving region 216 or an artifact-containing region 402 is classified as an artifact-free region 404. As can be seen from FIG. 4, the artifact-containing regions 402 fall entirely within the soft tissue portion 312 of the segmented reconstructed imaging data 214Z. That is, the soft tissue portion 312 lies within either the artifact-containing region 402 or the artifact-free region 404. The artifact-free region 404 includes not only some of the soft tissue 312, but also the bone 306, the liver 308, and the kidneys 310.

One or more class divisions of imaging data are then defined 224 for application within the artifact-containing regions 222. Each of the classes is defined by mutually exclusive ranges of attenuation value coefficients, set by different minimum and maximum values per class. The number of classes, and the range of values within each class, will in general depend on which of the segmented data groups 214 appear in the regions 222. For example, in FIG. 3, the artifact-containing regions 222 are composed solely of the soft tissue 312 segmented data group. More generally, however, the regions 222 may also be large enough to encompass different types of segmented data groups 214, such as both soft tissue 312 and liver 308. Each one of the segmented data groups 214 which falls within an artifact-containing region 222 is separately divided into one or more classes.

FIG. 3 represents the simplest scenario, where there is only one such segmented data group 214, which in that case is soft tissue 312. It may be convenient to treat all of the soft tissue 312 under only one class 224. For example, if there is very little variation in attenuation coefficient values among the soft tissue 312 both inside and outside the regions 222, there is little benefit to treating more dense areas of soft tissue 312 differently from less dense areas of soft tissue 312. More often, however, there will be a significant variation in attenuation coefficient values among the soft tissue 312 both inside and outside the regions 222. In that more typical situation, it will often be convenient to divide the soft tissue 312 into three classes corresponding respectively to water (lowest attenuation), fat (medium attenuation), and muscle (highest attenuation).

More generally, however, the artifact-containing regions 222 may cover more than one of the segmented regions 214 of imaging data. In that event, each one of the segmented regions 214 must be separately analyzed to determine whether further classification of that region would be useful and, if so, what that classification might be.

The number of classes, as well as the minimum and maximum values of each class, may be defined in many different ways. In a first embodiment, the classes are pre-defined before any imaging data 206 is acquired 204. That is, the classification division 224 can take into account prior knowledge about the anatomy and typical attenuation coefficients of the various regions of interest. Such knowledge can be solely used to determine the number of classes and to define the ranges of the classes.

In a second embodiment, the classes of a segmented data group 214 are defined at least in part by analyzing the reconstructed imaging data 210 assigned to that group 214. This may be done, for example, by applying a fuzzy segmentation and classification analysis to the imaging data of the group 214 which is located within the artifact-free region 404. Thus, if there is very little variation in attenuation coefficient values among the soft tissue 312 throughout the entire artifact-free region 404, then classification may be omitted entirely. Data from the artifact-free region 404 is used so as to avoid corruption which may be caused by relying on data from the artifact-containing regions 402. In further embodiments, the data group 214 classes may be defined using knowledge and experience gained both before and after the recording of imaging data from an imaging scan of a particular patient.

Each image data class is then associated 226 with one or more representative attenuation coefficients. In one embodiment, each representative attenuation coefficient is defined simply as the mean of the class's minimum and maximum attenuation coefficient values. In an alternative embodiment, each representative attenuation coefficient is some other single pre-defined value per class, which may be determined independently of or as a partial result of the segmented reconstructed imaging data 214. In yet a further embodiment, each class may be constrained to have an attenuation coefficient which falls within a range of values. The representative attenuation coefficient range may be defined to be the minimum and maximum values which define the class, or some smaller range which fits within that class definition.

Each three-dimensional voxel of reconstructed image data 210 within the artifact-containing regions 402 is assigned 228 to one of the image data classes using known methods. For example, Mohamed N. Ahmed et al., "A Modified Fuzzy C-Mcans Algorithm for Bias Field Estimation and Segmentation of MRI Data", *IEEE Transactions on Medical Imaging*, vol. 21, no. 3 (March 2002) identifies a similar method which may be applied to the present context. The disclosure of Ahmed et al. is fully incorporated herein by reference.

The next step of the method 200 determines 230 a local bias field 232 within the artifact-containing region 402. The local bias field 232 describes, for each voxel within the region 402, the difference between the reconstructed voxel attenuation value 210 and the expected voxel attenuation value according to the classification assignment 228. In other words, the local bias field 232 identifies the error introduced to the reconstructed voxel values 210 by motion artifacts, assuming that the true values are provided by the classification assignment 228. If the representative attenuation coefficient of the class is a single number, then the local bias field 232 entry is defined as the difference (including positive/negative direction) between the reconstructed value and the representative value. If the representative attenuation coefficient of the class is a range of values, then the local bias field 232 entry is defined as zero if the reconstructed value falls within the range, or otherwise the difference (including positive/negative direction) between the reconstructed value and the closer of the maximum or the minimum of the range. The local bias field determination 230 can include a smoothing step that favors smoothness of the local bias field 232 and reduces noise. Alternatively, or in addition, the local bias field 232 can be locally regularized in order to favor the locally expected shape of the artifacts. Such expected motion artifact shapes may, for example, be line-like or have defined directional characteristics.

Motion artifacts within the reconstructed imaging data 210 are then reduced by applying 234 the local bias field 232 to the artifact-containing regions 402 of the reconstructed imaging data 210. The local bias field 232 is applied inside the artifact-containing regions 402 to visibly reduce motion artifacts. Application of the local bias field can be configured to have a gradual weighting region around its boundaries, such that no sudden steps are introduced around the affected region by the local bias field 232 application. Limiting the correction to the artifact-containing regions 402 reduces the overall risk of applying the method, as most regions of the reconstructed imaging data 210 are not affected by the correction.

The application 234 generates motion-corrected reconstructed imaging data 236. If the application 234 also removed the segmented bowel gas pocket regions 216/304 from the imaging data, those regions may be re-inserted into the imaging data in order to produce the final image 236.

Although methods have been described for the specific case 200 of reducing motion artifacts due to bowel gas movement, the methods may easily be applied to other localized artifacts. Such other localized artifacts include, for example, scatter-induced streaks off bones, artifacts from detector imperfections, and other localized artifacts.

Taking bone streak artifacts as an example, the first steps 202 through 210 of a bone streak artifact correction method 200' are identical to the motion artifact correction method 200. The segmentation step 212', however, would include at least the identification of bone regions 306 within the reconstructed imaging data 210. The resulting segmented reconstruction data 214 is then divided into suspect bone regions 216' and non-bone regions 218', rather than suspect moving regions 216 and non-moving regions 218. In general, the segmentation step of the method identifies suspect regions within the data 214 near which the localized artifacts of interest are expected to occur. Moving objects create localized motion artifacts, and bone tissue creates bone streak artifacts.

Turning to the definition 220' of artifact-containing regions 222, bone streak artifacts are assumed to originate from the suspect bone regions 216'. Therefore, it is to be expected that the bone streak artifacts are generally decreasing in magnitude with increasing distance from the suspect bone regions 216'. Thus, the definition step 220' seeks to define the portions of the segmented reconstructed imaging data 214 which may be affected by bone streak artifacts. The inner boundary or boundaries of each artifact-containing region 222 correspond(s) to the suspect bone regions 216' identified in the segmentation step 212'. The outer boundary of each artifact containing region 222 is determined by the step 220', as already described above in relation to motion artifacts. The artifact-containing region definition step 220' may further take into account the special characteristics of scatter-induced streaks off of bone. For example, many bone streak artifacts have a line-like appearance radiating away from the suspect bone regions 216', so the step 220' may pay special attention to such features within the segmented reconstructed imaging data 214.

Figure 5:
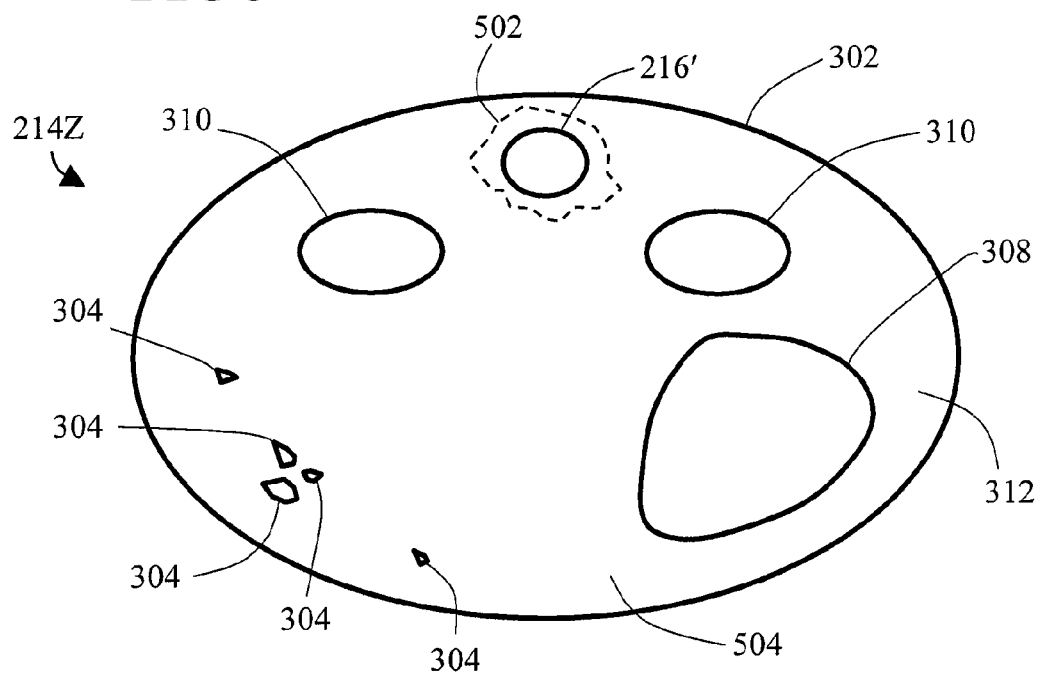
FIG. 5 is a schematically representative illustration of segmented reconstruction data including defined artifact-containing regions surrounding bone regions.

FIG. 5 is a schematically representative illustration of segmented reconstructed imaging data 214 including defined artifact-containing regions. FIG. 5 is the same two-dimensional cross-section 214Z as shown in FIG. 3. In FIG. 5, the data 214Z is divided into three classes: the suspect bone regions 216', the artifact-containing regions 502, and the artifact-free regions 504. The suspect bone regions 216' comprise each of the regions from the segmentation 212 that were classified as bone regions 306. Each of those suspect bone regions 216' is then surrounded by artifact-containing regions 502 as determined in step 220', which are shown by dotted lines in FIG. 5. Then, all other imaging data which is not a suspect bone region 216' or an artifact-containing region 502 is classified as an artifact-free region 504. As can be seen from FIG. 5, the artifact-containing regions 502 fall entirely within the soft tissue portion 312 of the reconstructed imaging data 214Z. That is, the soft tissue portion 312 lies within either the artifact-containing region 502 or the artifact-free region 504. The artifact-free region 504 includes not only some of the soft tissue 312, but also the bowel gas pockets 304, the liver 308, and the kidneys 310.

The remaining steps 224 to 234 of the bone streak artifact correction method 200' proceed in the same manner as the motion artifact correction method 200 described above. The result is a set of reconstructed imaging data 236' which is corrected for localized bone streak artifacts.

In yet additional embodiments, the present methods can be used to notify a user that imaging data may contain localized artifacts such as motion artifacts, bone streak artifacts, or other such artifacts. The user notification may take many forms. In one embodiment, the system may simply notify the user that imaging data which the user is accessing may contain localized artifacts. In another embodiment, the system may additionally present the user with an artifact-corrected reconstructed imaging data set. In a further embodiment, the system may identify one or more regions within a corrected or un-corrected reconstructed image data set which may be corrupted by localized artifacts, to indicate regions of lower confidence. In addition, the estimated bias field or a derived measure can be presented to the user as a local measure of confidence together with the reconstructed imaging data to further quantify regions of possibly low confidence.

The invention has been described with reference to the several embodiments. Obviously, modifications and alterations will occur to others upon reading and understanding the preceding detailed description. It is intended that the invention be construed as including all such modifications and alterations insofar as they come within the scope of the appended claims or the equivalents thereof The invention may take form in various compositions, components and arrangements, combinations and sub-combinations of the elements of the disclosed embodiments.

Having thus described several embodiments, the invention is now claimed to be:

1. A method for reducing localized artifacts in imaging data, the method comprising:
    segmenting the imaging data to identify one or more suspect regions in the imaging data near which localized artifacts are expected to occur;
    defining an artifact-containing region of interest in the imaging data around each suspect region;
    defining one or more classes for the imaging data of the artifact-containing regions of interest, and associating each class with at least one representative imaging value;
    assigning each item of imaging data within the artifact-containing regions to one of the classes;
    determining a local bias field within the artifact-containing regions describing, for each item of imaging data within the artifact-containing regions, a difference between a calculated imaging value and the representative imaging value based on the classification; and
    applying the local bias field to the imaging data within the artifact-containing regions to produce an artifact-corrected imaging data.

2. The method of claim 1, wherein the imaging data comprises a reconstructed imaging data.

3. The method of claim 1, wherein the segmentation step comprises an application of one or more thresholds to the imaging data.

4. The method of claim 3, wherein at least one inner boundary of each artifact-containing region is defined as an outer boundary of a suspect region.

5. The method of claim 4, wherein an outer boundary of each artifact-containing region is defined by a region growing technique starting at the inner boundary as a seed point, and applying a stopping criterion.

6. The method of claim 5, wherein the stopping criterion comprises a normal range of values for imaging data which surround the suspect region.

7. The method of claim 1, further comprising at least two classes for the imaging data of the artifact-containing regions of interest, defined by mutually exclusive minimum and maximum class values.

8. The method of claim 7, further comprising defining a number of the classes and the minimum and maximum class values before the imaging data is acquired (204).

9. The method of claim 7, further comprising defining a number of the classes and the minimum and maximum class values at least in part by analyzing the imaging data.

10. The method of claim 7, wherein the artifact-containing region classification comprises a first lowest value class, a second medium value class, and a third high value class.

11. The method of claim 1, wherein the representative imaging value is a single value, and the local bias field identifies a difference between the calculated imaging value and the representative imaging value.

12. The method of claim 1, wherein the representative imaging values are a range of values defined between a minimum value and a maximum value, and the local bias field is defined as zero if the calculated imaging value falls within the range, or otherwise as a difference between the calculated imaging value and the maximum value or the minimum value of the range.

13. The method of claim 1, wherein the local bias field determination comprises a smoothing step that favors a smoothness of the local bias field and reduces noise.

14. The method of claim 1, wherein the localized artifacts comprise motion artifacts, and the suspect regions correspond to imaged objects which are suspected to cause motion artifacts.

15. The method of claim 1, further comprising providing a notification that the imaging data may contain the localized artifacts.

16. The method of claim 15, wherein the notification comprises an identification of one or more regions within the imaging data which may be corrupted by localized artifacts.

17. An image processing system comprising logic stored on a memory, wherein the logic provides instructions for reducing localized artifacts in imaging data, the instructions comprising:
    segmenting the imaging data to identify one or more suspect regions in the imaging data near which localized artifacts are expected to occur;
    defining an artifact-containing region of interest in the imaging data around each suspect region;
    defining one or more classes for the imaging data of the artifact-containing regions of interest, and associating each class with at least one representative imaging value;
    assigning each item of imaging data within the artifact-containing regions to one of the classes;
    determining a local bias field within the artifact-containing regions describing, for each item of imaging data within the artifact-containing regions, a difference between a calculated imaging value and the representative imaging value based on the classification; and
    applying the local bias field to the imaging data within the artifact-containing regions to produce an artifact-corrected imaging data.

18. The system of claim 17, wherein the imaging data comprises a reconstructed imaging data.

19. The system of claim 17, wherein the segmentation step comprises an application of one or more thresholds to the imaging data.

20. The system of claim 19, wherein at least one inner boundary of each artifact-confining region is defined as an outer boundary of a suspect region.

21. The system of claim 20, wherein an outer boundary of each artifact-containing region is defined by a region growing technique starting at the inner boundary as a seed point, and applying a stopping criterion.

22. The system of claim 21, wherein the stopping criterion comprises a normal range of values for imaging data which surround the suspect region.

23. The system of claim 17, further comprising at least two classes for the imaging data of the artifact-containing regions of interest, defined by mutually exclusive minimum and maximum class values.

24. The system of claim 23, further comprising defining a number of the classes and the minimum and maximum class values before the imaging data is acquired (204).

25. The system of claim 23, further comprising defining a number of the classes and the minimum and maximum class values at least in part by analyzing the imaging data.

26. The system of claim 23, wherein the artifact-containing region classification comprises a first lowest value class, a second medium value class, and a third high value class.

27. The system of claim 17, wherein the representative imaging value is a single value, and the local bias field identifies a difference between the calculated imaging value and the representative imagine value.

28. The system of claim 17, wherein the representative imaging values are a range of values defined between a minimum value and a maximum value, and the local bias field is defined as zero if the calculated imaging value falls within the range, or otherwise as a difference between the calculated imaging value and the maximum value or the minimum value of the range.

29. The system of claim 17, wherein the local bias field determination comprises a smoothing step that favors a smoothness of the local bias field and reduces noise.

30. The system of claim 17, wherein the localized artifacts comprise motion artifacts, and the suspect regions correspond to imaged objects which are suspected to cause motion artifacts.

31. The system of claim 17, further comprising providing a notification that the imaging data may contain the localized artifacts.

32. The system of claim 31, wherein the notification comprises an identification of one or more regions within the imaged data which may be corrupted by localized artifacts, to indicate regions of lower confidence.

33. An image processing system comprising logic stored on a memory, wherein the logic provides instructions for reducing bone streak artifacts in imaging data, the instructions comprising:
- segmenting the imaging data to identify one or more bone regions in the imaging data near which localized artifacts are expected to occur;
- defining an artifact-containing region of interest in the imaging data around each bone region;
- defining one or more classes for the imaging data of the artifact-containing regions of interest, and associating each class with at least one representative imaging value;
- assigning each item of imaging data within the artifact-containing regions to one of the classes;
- determining a local bias field within the artifact-containing regions describing, for each item of imaging data within the artifact-containing regions, a difference between a calculated imaging value and the representative imaging value based on the classification; and
- applying the local bias field to the imaging data within the artifact-containing regions to produce a bone artifact-corrected imaging data.

34. The system of claim 33, wherein the artifact-containing region definition step attempts to identify imaging portions having a line-like appearance radiating away from the bone regions.

* * * * *